United States Patent [19]

Ouchi et al.

[11] Patent Number: 4,589,403
[45] Date of Patent: May 20, 1986

[54] APPARATUS FOR CLEANING AND STERILIZING A GUIDE TUBE FOR A FORCEPS-CONTROL MEMBER OPERATING WIRE IN AN ENDOSCOPE

[75] Inventors: Teruo Ouchi, Kawagoe; Kazukiyo Tamada, Kawaguchi; Shiyouichi Yamaka, Kamifukuoka, all of Japan

[73] Assignee: Kabushiki Kaisha Medos Kenkyusho, Japan

[21] Appl. No.: 653,828

[22] Filed: Sep. 24, 1984

Related U.S. Application Data

[63] Continuation of Ser. No. 433,671, Oct. 12, 1982, abandoned.

[30] Foreign Application Priority Data

Oct. 13, 1981 [JP] Japan ................................ 56-152523

[51] Int. Cl.⁴ ............................................. A61B 1/00
[52] U.S. Cl. ............................................ 128/4
[58] Field of Search ........................... 128/4–8; 134/167 R, 167 C, 175, 177

[56] References Cited

U.S. PATENT DOCUMENTS 3,924,608 12/1975 Mitsui ..................... 128/4
3,959,840 6/1976 Sato .................... 134/167 C
4,190,041 2/1980 Chikama .................. 128/4

FOREIGN PATENT DOCUMENTS 2828638 1/1979 Fed. Rep. of Germany .......... 128/6

*Primary Examiner*—Edward M. Coven
*Assistant Examiner*—Max F. Hindenburg
*Attorney, Agent, or Firm*—Steinberg & Raskin

[57] ABSTRACT

An endoscope includes a forceps-control member movably mounted in a forward region of the elongate portion which is adapted to be inserted into a body cavity for selectively projecting and retracting forceps from and into the forward region of the insertion portion and an operating wire having one end connected to the forceps-control member and extending to the manipulator unit through an operating wire guide tube such that the projection and retraction of the forceps is controlled from the manipulator unit through the displacement of the operating wire. Apparatus for cleaning and/or sterilizing the operating wire guide tube includes a control shaft guide tube connected to the wire guide tube, a tubular control shaft mounted for movement within the control shaft guide tube, the control shaft being connected to the other end of the operating wire, a fluid passage provided in the tubular control shaft communicating with the control shaft guide tube, a flexible tube one end of which is connected to the tubular control shaft and communicating with the fluid passage, the flexible tube including a slackened length portion, and a fluid inlet externally provided on the manipulator unit of the endoscope, the other end of the flexible tube communicating with the fluid inlet.

9 Claims, 4 Drawing Figures

APPARATUS FOR CLEANING AND STERILIZING A GUIDE TUBE FOR A FORCEPS-CONTROL MEMBER OPERATING WIRE IN AN ENDOSCOPE

This is a continuation of application Ser. No. 433,671 filed 10/12/82, now abandoned.

BACKGROUND OF THE INVENTION

This invention relates generally to endoscopes and, more particularly, to improvements in apparatus for cleaning and sterilizing a guide tube for a forceps-control member operating wire in an endoscope.

It is well known that when a forceps-control member, for example a so-called forceps-riser, is raised and allowed to be lowered or collapsed through the manipulation of an operating wire to perform various operations in connection with a biopsy, i.e., an inspection of living tissue, fluid secreted from the body, such as gastric juice or mucus and blood, often invades the interior of the wire guide tube through its forward opening.

Thus, generally, biopsy operations wherein a sample of living tissue is removed from the tissue of a body cavity, have recently been accomplished using endoscopes which are adapted to perform such operations in addition to the usual observations and diagnosis generally performed during inspections using endoscopes. Accordingly, modern endoscopes are generally provided with a picker, such as forceps, for partially removing living tissue from the wall of a body cavity or organ, a forceps-control member, such as a riser mounted in a forward region of the portion of the endoscope which is introduced into the body cavity for controlling the orientation of the picker, an operating wire connected to the forceps-control member for movably driving the same, a guide tube through which the operating wire passes to guide the latter to a manipulator unit, and a control mechanism connected to an end of the operating wire mounted on or in the manipulator unit which is manually operated to pull or slacken the operating wire to thereby raise the forceps-control member or allow the same to collapse.

However, as mentioned above, it is inevitable that fluids secreted from the body, blood or the like, will enter or invade the interior of the guide tube through the small gap defined between the operating wire and the wire guide tube under the effect of pressure present within the body cavity created during the manipulation of the instrument to direct the picker, e.g. the forceps, onto the precise desired location in the body cavity. In particular, the secreting fluid, blood or the like, will invade the interior of the guide tube along the plies of the stranded operating wire as the latter is pulled.

In an attempt to overcome this problem, an arrangement is disclosed in Japanese Utility Model Laid-Open Application No. 1976-38986 wherein the operating wire guide tube is provided along its inner periphery at the front end thereof with a suitable sealing member by which the fine gap present between the guide tube and the operating wire is sealed. However, it has been found that the sealing of the gap using such an arrangement in practice results in an increase in the load exerted on the operating wire during its movement resulting in an obstruction in the smooth manipulation of the wire and consequently adversely affecting the maneuverability of the endoscope as a whole. It has also been found that such gap sealing arrangement cannot completely seal the interior of the wire guide tube from the secreting fluid, blood or the like, along the plies of the stranded operating wire. More disadvantageously, use of the gap sealing arrangement disclosed in the above-mentioned Japanese application has shown that the sealing member prevents cleaning and sterilizing liquid for the secreting fluid, blood or the like from flowing smoothly within the wire guide tube thereby rendering an efficient cleaning and sterilization thereof impossible.

The introduction or invasion of secreting fluid, blood or the like along the operating wire into the wire guide tube which occurs when the picker, such as forceps, is manipulated is extremely undesirable for the following reasons. Thus, such fluid will cause the wire to rust and, additionally, will cause a clogging of the guide tube when the fluid dries thereby preventing the operating wire extending therethrough from being smoothly moved. In extreme cases, invasion of secreted fluids, blood and the like into the guide tube will continue into the manipulator unit whereupon both the interior as well as the exterior of the manipulator unit will become contaminated by the fluid causing subsequent manipulation of the unit to become more difficult. The invasion of such body fluids is also undesirable from the medical viewpoint in that after the endoscope is used with a patient who is syphilitic, Autrali antigen positive or the like, use of the same endoscope in another patent may cause that disease to be transmitted to the new patient. In order to avoid this danger, both the exterior and the interior of the endoscope must be cleaned and sterilized prior to every use or, at the least, quite often. Such cleaning and sterilization is more easily achieved with higher efficiencies when the quantity of secreting body fluid, blood or the like which invades the guide tube can be reduced. Accordingly, it is desirable to maintain the quantity of such secreting fluid, blood or the like which invades the guide tube at a minimum.

In order to most efficiently eliminate the invasion of fluids into the guide tube as described above, it might be proposed to reduce the inner diameter of the guide tube relative to the diameter of the operating wire to the extent possible so long as the load resisting the movement of the operating wire is not thereby increased to an unacceptable level. However, it must be kept in mind that the reduction of the inner diameter of the guide tube relative to the diameter of the operating wire will disadvantageously obstruct a smooth flow of cleaning and sterilizing liquid through the guide tube. In this connection, in order to prevent the secreting fluid, blood or the like which has invaded the guide tube from further movement into the manipulator unit from which it can then leak to the exterior as well as to facilitate the discharge of the fluid which has invaded into the endoscope during the rinsing operation, it has been proposed to provide a hollow room within the manipulator unit, which room is provided with a piston-like slidable member for preventing leakage of the liquid, the end of the operating wire being operatively associated with the slidable member. An opening is also provided in the hollow room which communicates with the exterior of the manipulator unit for a rinsing operation. This arrangement inhibits the flow of fluid which has invaded the guide tube from further flow into the hollow room and subsequently leaking therefrom to the exterior of the manipulator unit and also allows the fluid remaining in the hollow room to be discharged through the opening to the exterior for rinsing. Moreover, rinsing liquid can be injected through the opening into the hollow room and the guide tube to thereby achieve a desired rinsing or cleaning effect.

However, this arrangement also presents problems in that movement of the operating wire for effecting the raising or collapsing of the forceps-control member, e.g. the forceps-riser, which is connected to the wire and, therefore, the orientation of the picker, e.g. the forceps, necessarily relies upon the reciprocating motion of the piston-like member for prevention of leakage. However, each stroke of the piston-like member results in the secreting fluid, blood or the like being sucked from or forced into the guide tube through the opening or gap at the forward end of the guide tube resulting in the invasion of the secreting fluid, blood or the like being unexpectedly promoted by the arrangement.

It is also well known to provide a channel in communication with the hollow room through control means, such as a communication control valve, to supply water or air thereto primarily for cleaning a location to be inspected. Thus, this separate channel may be utilized for a desired rinsing or cleaning operation. However, such a water or air supply channel usually has opposed ends which are opened so that the small gap defined between the guide tube and the operating wire extending therethrough cannot produce a sufficiently high resistance within the tube to increase the inner pressure during injection of the rinsing liquid so as to maintain a smooth flow of the rinsing liquid through the gap between the wire and the guide tube. Thus, an adequate rinsing effect cannot be expected using this arrangement.

With respect to the effect of variations in the inner diameter of the wire guide tube on the flow rate of manually injected rinsing water, tests have been conducted the results of which are illustrated in FIG. 4 which graphically illustrates the flow rate of cleaning water versus the inner diameter of the guide tube for the operating wire. In this experiment, the operating wire constituted by a stranded wire having an outer diameter of 0.63 mm was used. The inner diameter of the wire guide tube was varied from 0.8 mm through 0.85 mm, 0.9 mm, 0.95 mm to 1.05 mm. The results of the experiment are set forth in the following table:

| Inner diameter of guide tube | Injected flow rate/min. |
| --- | --- |
| 0.8 mm | 12 c.c. |
| 0.85 mm | 19 c.c. |
| 0.9 mm | 26 c.c. |
| 0.95 mm | 30 c.c. |
| 1.05 mm | 40 c.c. |

In the experiment, the rinsing water was injected by an injection pump under a manual pressure. As the results shown in FIG. 4 and the above table indicate, although it is preferable to minimize the cross-sectional area of passage defined between the outer surface of the operating wire and the inner surface of the wire guide tube in order to suppress the quantity of the secreting fluid, blood or the like which may invade the wire guide tube through the end thereof, an excessive reduction of this sectional passage area at the same time will constrict the sectional passage area through which the injected rinsing water passes thereby making the desired injection difficult. Accordingly, it will be understood from these test results that are pointed out above the passage resistance within the guide tube would not be sufficiently high to obtain the desired rinsing effect even when the wire guide tube communicates with the separate water or air supply channel, which usually has a relatively large diameter, so as to rinse the interior of the wire guide tube by injecting rinsing water through that separate channel, since the latter is usually not a closed tube but, rather, generally comprises a tube having open opposite ends. The results of the experiment indicate that the inner diameter of the guide tube should preferably be on the order of about 0.8 mm or greater when a stranded wire having an outer diameter of 0.63 mm is used in order to obtain a smooth flow of water through the wire guide tube under manual pressure. In this case, the sectional passage area will be on the order of about 0.17 mm$^2$. The experiment indicates that when the sectional passage area is less than about 0.17 mm$^2$, the force required for injecting rinsing water becomes too large to allow for the desired maneuverability.

Thus, as indicated above, in order to minimize the invasion of secreting fluid, blood or the like into the wire guide tube through the fine gap formed at its forward end, the sectional passage area must be as small as possible, such reduction in the sectional area being limited to a reasonable degree by considerations of maneuverability during rinsing or cleaning operations. In practice, the inner pressure within the body cavity and the capillary phenomenon which occurs along the plies of the stranded operating wire make it difficult to entirely suppress invasion of the secreting fluid, blood or the like into the guide tube. Moreover, it is extremely important to avoid the phenomenon wherein the necessary manipulation for controlling the orientation of the picker, such as forceps, produces a negative pressure within the guide tube through motion of the piston-like member as discussed above.

SUMMARY OF THE INVENTION

Accordingly, a principal object of the present invention is to provide a new and improved device in an endoscope for the cleaning and sterilization of a guide tube for a forceps-control member operating wire.

Another object of the present invention is to provide a new and improved device for cleaning and sterilization of a guide tube for a forceps-control member operating wire which is so constructed that the invasion of secreting fluid, blood and the like into the guide tube can be minimized and so that cleaning or sterilizing fluid can easily flow through the wire guide tube without any significant residue of such fluid remaining in the guide tube when it is desired to clean or sterilize the latter.

Still another object of the present invention is to provide a new and improved apparatus for cleaning and sterilization of a guide tube for a forceps-control operating wire wherein neither the gap within the guide tube nor the hollow room extending in continuity with the guide tube increases as the operating wire is pulled to avoid promotion of fluid invasion into the guide tube.

Yet another object of the present invention is to provide a new and improved apparatus for cleaning and sterilizing a guide tube for a forceps-riser operating wire wherein a passage through which rinsing or cleaning water is directly injected into the guide tube contains no bends which would present a resistance to the flow thereof to thereby obtain a high efficiency cleaning and sterilization.

Briefly, in accordance with the present invention, these and other objects are provided in an endoscope which includes a manipulator unit and a forward elongate insertion portion extending from the manipulator unit adapted to be inserted into a body cavity, forceps-control means movably mounted in a forward region of the insertion portion for selectively projecting and retracting forceps from and into the forward region of the insertion portion, an operating wire guide tube extending within the insertion portion towards the manipulator unit, and an operating wire extending through and being guided by the wire guide tube, one end of the operating wire being connected to the forceps-control means whereby the projection and retraction of the forceps can be controlled from the manipulator unit through displacement of the operating wire. The apparatus for cleaning and/or sterilizing the operating wire guide tube comprises a control shaft guide tube connected to the wire guide tube, a tubular control shaft mounted for movement within the control shaft guide tube, the control shaft being connected to the other end of the operating wire. Fluid passage means are provided in the tubular control shaft which communicates with the control shaft guide tube and a flexible tube is provided having a first end which is connected to the tubular control shaft communicating with the fluid passage means, the flexible tube including a slackened length portion. Fluid inlet means are provided externally on the manipulator unit with the second end of the flexible tube communicating therewith for injecting cleaning fluid or the like into the flexible tube.

Sealing means in the form of an O-ring may be provided to achieve a substantially fluid-tight seal between the tubular control shaft and the control shaft guide tube.

The fluid passage means are preferably constituted by a passage formed in the tubular control shaft, one end of which opens rearwardly of the O-ring and communicates with the flexible tube while the other end of the passage opens forwardly of the sealing means and communicates, preferably through radial openings formed in the tubular control shaft, with the control shaft guide tube.

The slackened length portion of the flexible tube preferably comprises a surplus length portion or the flexible tube which has a wound configuration.

DESCRIPTION OF THE DRAWINGS

A more complete appreciation of the present invention and many of the attendant advantages thereof will be readily understood by reference to the following detailed description when considered in connection with the accompanying drawings in which.

DESCRIPTION OF THE PREFERRED EMBODIMENTS

Figure 1:
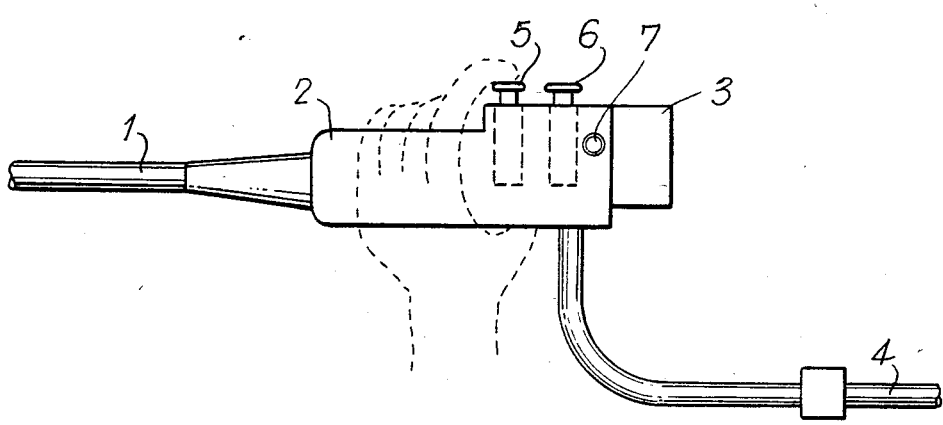
FIG. 1 is a partial schematic view of an endoscope incoporating the apparatus of the present invention.
Figure 4:
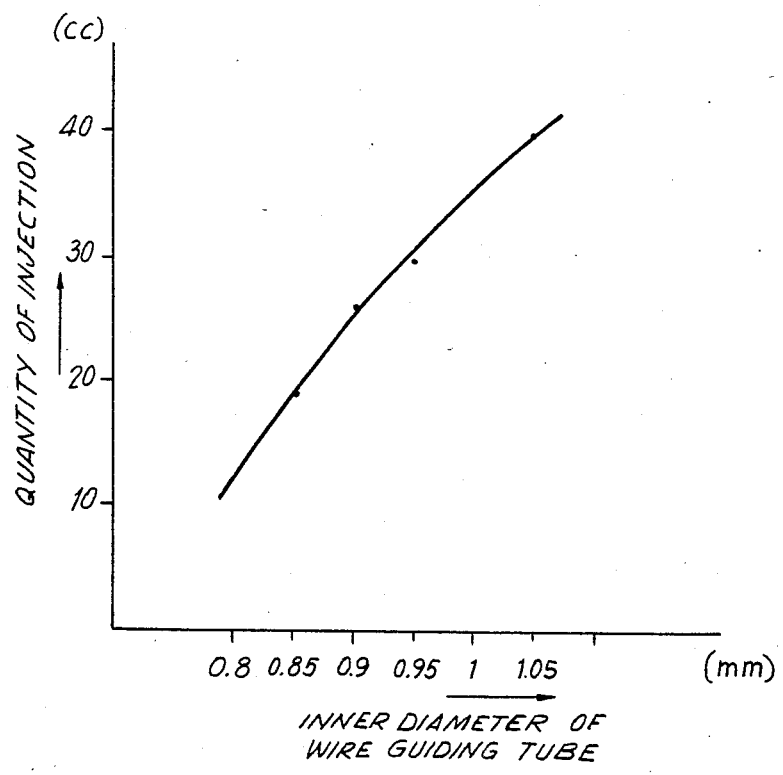
FIG. 4 is a graphic illustration showing experimental test results wherein the flow rate of cleaning water versus the inner diameter of the operating wire guide tube is shown.

Referring now to the drawings wherein like reference characters designate identical or corresponding parts throughout the several views, and more particularly to FIG. 1, an endoscope incorporating apparatus in accordance with the present invention includes a manipulator unit 2 and a forward elongate insertion portion 1 extending from the manipulator unit 2 and which is adapted to be inserted into a body cavity. An ocular unit 3 is connected to the rear end of the manipulator unit 2 and a connector unit 4 extends to a light source (not shown). The manipulator unit 2 is provided with a button 5 which operates a valve for controlling an air/water supply and a button 6 which operates a valve for providing suction. These endoscope features are generally known in the prior art. Other components of the endoscope such as the forceps and a knob for manipulating a forceps-control member, hereinafter referred to as a forceps-riser, are not shown in FIG. 1. A mouthpiece 7 for injecting water and sterilizing fluid for cleaning and sterilizing the components of the endoscope, respectively, is provided on the side of the manipulator unit 2.

Figure 2:
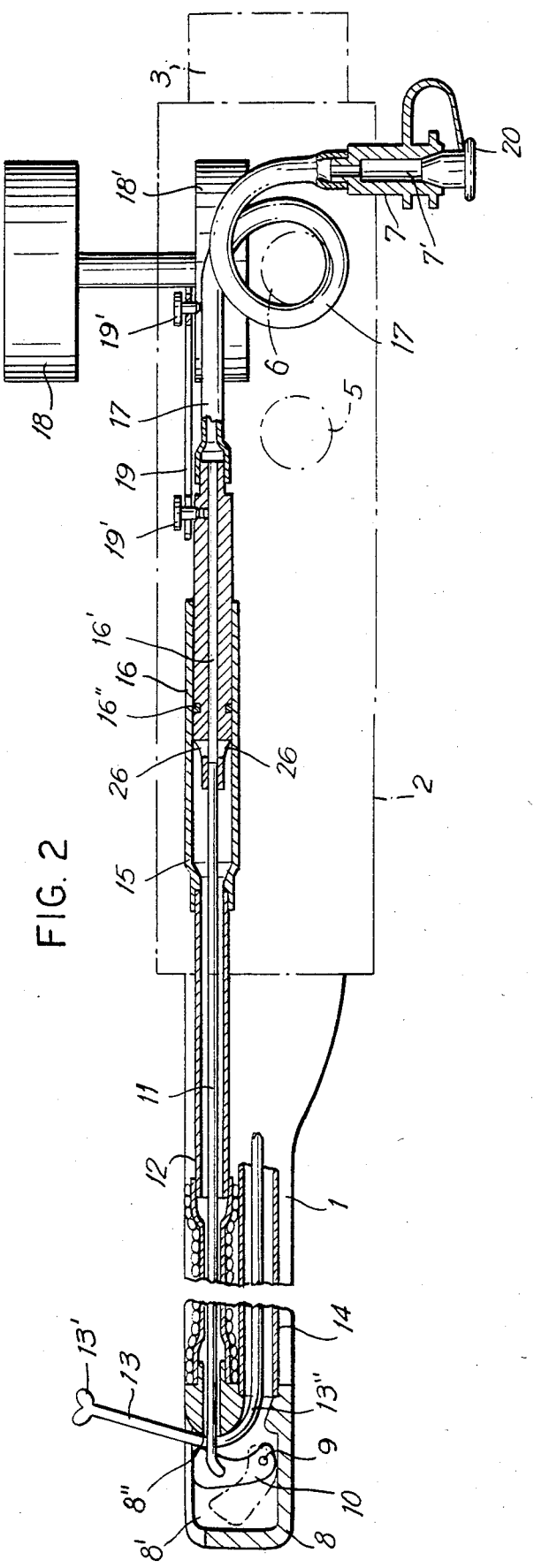
FIG. 2 is a side elevation view in section of an endoscope incorporating apparatus in accordance with the present invention.

Referring now to FIG. 2, metallic fittings 8 are mounted on the forward tip of the elongate portion 1. A forceps-riser 10 is pivotally mounted within the hollow interior 8' of the metallic fittings 8. In the illustrated embodiment, the forceps-riser 10 is mounted on a pivot pin 9 so as to movable from a lowered or collapsed position illustrated in phantom to a raised position shown in solid lines. One end of a manipulating or operating wire 11 is connected to the forceps-riser 10 and is guided through a guide tube 12 along the elongated portion 1 of the endoscope to the manipulator unit 2. The forceps-riser 10 may thus be rotatably raised by pulling the wire 11 and rotatably collapsed or lowered by slackening the wire 11 at the manipulator unit 2. The guide tube 12 also functions to prevent any liquid, such as secreted fluid, blood and the like, which has entered into the guide tube 12 through the fine gap or opening 8" at the tip of the endoscope from further entering into the interior of the elongated portion 1. The forward end of guide tube 12 is tightly connected to the metallic fittings 8.

The endoscope includes forceps 13 which function to remove a part of living tissue from the body for endoscopic biopsy, the forceps including a tip formed as a picker 13' and a flexible portion 13" adjoining the picker 13'. The flexible forceps portion 13" bears against one side of the forceps-riser 10 so that the orientation of the picker 13 can be varied in a controlled manner as the forceps-riser 10 is raised or collapsed. Such mechanism is substantially identical to those used in endoscopes of the prior art. A channel 14 is provided through which the flexible portion 13" is guided and which, like the guide tube 12, extends to the manipulator unit 2, the rearward portions of the channel 14 being omitted from FIG. 2 for the sake of clarity.

A guide tube 15 is tightly connected to the rear end of the operating wire guide tube 12 and serves to guide the movement of a tubular control shaft 16 described below in greater detail. The operating wire 11 extends from the wire guide tube 12 into the control shaft guide tube 15 and is integrally connected at its rearward end to the tubular control shaft 16 which partially extends around the terminal portion of the operating wire 11. The tubular control shaft 16 is at least partially enclosed within the guide tube 15 for slidable movement therein. An O-ring 16" is mounted around the outer periphery of a forward region of the tubular control shaft 16 to maintain sealing engagement with the inner wall of the control shaft guide tube 15.

Fluid passage means are provided in the tubular control shaft 16 which communicate with the control shaft guide tube 15. The fluid passage means comprise a passage formed in the tubular control shaft, one end of which opens rearwardly of the O-ring 16" and the other end of which opens forwardly of the O-ring 16" and communicates with the control shaft guide tube 15. In the illustrated embodiment, the passage comprises a substantially axial cavity or bore 16' formed in the tubular control shaft 16 and which has a rearward end which opens from the rear end of the control shaft 16 rearwardly of O-ring 16" and at least one substantially radial opening 26 fluidly interconnecting the control shaft guide tube 15 and a forward portion of the axial bore or cavity 16' at a location forward of the O-ring 16". The passage comprising the axial bore or cavity 16' and openings 26 provides a means by which cleaning fluid can flow into and out from the tubular control shaft 16. More particularly, the cleaning fluid flows through the inner cavity 16' of the tubular control shaft 16 and then flows through the openings 26 into the interior of the guide tube 15 and then into the interior of the wire guide tube 12.

A length of flexible tube 17 has one end which is secured around the rear end of the tubular control shaft 16 so as to communicate with the cavity 16'. The flexible tube 17 has a slackened length portion which constitutes a surplus length thereof. The surplus length portion of flexible tube 17 has a wound configuration which may be wound around the suction button 6 as shown or, alternatively, around the air/water supply button 5. The other end of the flexible tube 17 is secured to the injection mouthpiece 7 constituting a fluid inlet means through which cleaning fluid or the like can be injected into the flexible tube 17. As seen in FIG. 2, the section of the flexible tube 17 which extends between the control shaft 16 and the looped or wound section of tube 17 is substantially coaxial with guide tube 15 and control shaft 16 and at the same time substantially tangential to the looped tube section.

Figure 3:
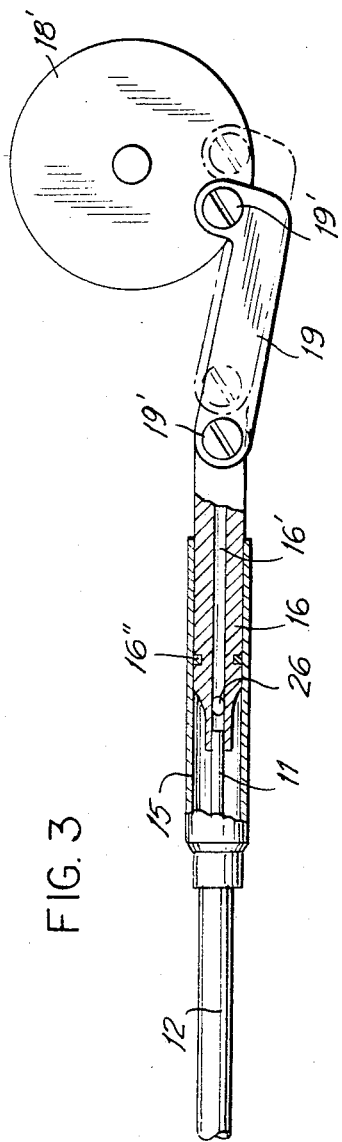
FIG. 3 is a plan view showing certain components of apparatus in accordance with the present invention and, in particular, illustrating a mechanism for manipulating the forceps-riser operating wire.

The manipulator unit 2 is externally provided with a knob 18 which is rotatably mounted in the manipulator unit 2 so as to operate a control mechanism by which the operating wire 11 can be selectively pulled or slackened through suitable rotation of knob 18. Referring to FIGS. 2 and 3, a disc 18' is situtated within the manipulator unit 2 and is mounted on a shaft which is common to the knob 18. A link 19 is pivotally connected at one of its ends to the disc 18' and is similarly pivotally mounted at its other end to the tubular control shaft 16. In the illustrated embodiment, pivot screws 19' accomplish the mounting of the opposite ends of link 19 to the disc and control shaft, respectively. As will be understood by reference to FIG. 3, rotation of the knob 18 will cause the tubular control shaft 16 to move in a linear manner within the guide tube 16 through the action of disc 18' and the connecting link 19 in a crank-like fashion. A stopper 20 normally closes the inlet 7' of the injection mouthpiece 7. The stopper 20 may be removed from the mouthpiece 7 to allow for the injection of cleaning fluid into the flexible tube 17. When the stopper 20 closes the mouthpiece 7 as shown in FIG. 2, it serves to prevent the entry of dust and other debris into the endoscope when the latter is stored. It will will be apparent from the above that the O-ring 16" reliably functions to prevent any liquid which has entered into the wire guide tube 12 from leaking between the inner wall of the control shaft guide tube 15 and the outer wall of the control shaft 16 to the exterior of the guide tube 15 even during the sliding movement of the tubular control shaft 16 along the inner wall of the guide tube 15 as knob 18 is rotated.

In the operation of conventional endoscopes, an external air supply device (not shown) is activated through the operation of the air supply button 5 so that the observation window (not shown) separately provided on the tip of the elongated portion 1 may be maintained at a position which is spaced from the inner wall of the body cavity in the course of use. However, the pressure created within the body cavity by the supply of air disadvantageously causes body liquids, such as secreting fluid produced in the body cavity, blood and the like, to be forcibly introduced through the opening 8" present in the tip of the endoscope into the fine gap defined between the operating wire 11 and the wire guide tube 12. The flexible portion 13" of forceps 13 which is guided by channel 14 is projected towards or retracted from the inner surface of the body cavity as the forceps-riser 10 is raised or collapsed within the interior of the metallic fittings 8. When so projected, the picker 13' bears against the inner wall of the body cavity and a separate manipulation causes the picker 13' to remove a part of the inner wall tissue for inspection purposes. The operation of pulling the operating wire 11 to raise the forceps-riser in connection with the direction of the picker 13' to the desired location on the inner wall of the body cavity acts to promote the invasion of the liquid material into the wire guide tube 12.

According to the present invention, even when the knob 18 is rotated so that the link 19 drives the tubular control shaft 16 from left to right as seen in FIG. 2 to thereby pull the wire 11 in the same direction, there will occur neither a substantial volume variation in the related area nor a collapse of the flexible tube 17, since the latter is also moved from left to right as the tubular control shaft 16 slidably moves in the guide tube 15 and such movement is accomplished so that the loop diameter of the tube portion of the loosely wound surplus length thereof does not significantly increase. Consequently, invasion of the liquid material into the wire guide tube 12 will not significantly increase during movement of the control shaft 16.

In order to remove any quantity of liquid material, such as secreting fluid, blood and the like, which has invaded the interior of the guide tube 12 and to simultaneously clean and/or sterilize the interior of the guide tube 12 and the various components associated therewith, an injector (not shown) filled with cleaning water or sterilizing fluid is connected to the injection mouthpiece 7 after the stopper 20 has been removed therefrom whereupon this liquid or fluid is injected through the inlet 7' into the mouthpiece 7 so that the cleaning water or sterilizing fluid flows through the flexible tube 17 and tubular control shaft 16 through the cavity 16' and openings 26 into the guide tubes 15 and 12 to thereby force any such quantity of liquid which has entered into the guide tube 12 and its associated components out of their interiors. In this manner, efficient cleaning and sterilization of the wire guide tube and associated components are achieved. Any cleaning water or sterilizing fluid remaining as a residue within the passage and guide tubes after the cleaning or sterilization operation can be easily removed by directing an air blast through the inlet 7' or, alternatively, by connecting a source of suction thereto.

As will be clearly understood from the foregoing, the apparatus according to the present invention permits a desired cleaning and sterilization to be easily achieved to prevent the formation of rust on wire 11 as well as to prevent clogging due to the hardening of liquid material, such as secreting fluid, blood and the like, around the operating wire 11. In this manner, smooth movement of the implements such as forceps 13 to be manipulated via the operating wire 11 is insured. Moreover, by incorporation the apparatus of the present invention is an endoscope, the same endoscope can be used for other patients after treating patients with infectious diseases of the type mentioned above. Another important advantage provided by the present invention is that the suction of liquid material, such as secreting fluid, blood and the like, through the open end of the guide tube 12 which might otherwise occur due to the manipulation of the wire 11 is now reduced to an acceptable degree so that at most only small quantities of liquid material can invade the guide tube 12 under the internal pressure within the body cavity. Moreover, such liquid material having a relatively high viscosity can be entirely prevented from invading the guide tube 12.

Still further, since there is no bend in the cleaning water or sterilization fluid passage, the water or fluid may flow in a linear manner through the guide tubes 12 and 15 and the tubular control shaft 16. This feature of the present invention also contributes to the prevention of corrosion of the operating wire 11 itself or at the connection between the wire 11 and the tubular control shaft 16 which might result in the accidental breakage of the wire 11 due to such corrosion. Since the injection mouthpiece 7 through which cleaning water or sterilizing fluid is injected is connected by way of the flexible tube 17 to the tubular control shaft 16 and is externally located at the rear side of the manipulator unit, the same will not present an obstruction to the manipulation of the endoscope during observation and diagnosis. Accordingly, this feature contributes to the realization of an endoscope which can be easily controlled with a high degree of maneuverability.

Regarding the stranded wire, the outer surface thereof can be preliminarily coated with a suitable plastic material in order to prevent the liquid material invading the guide tube 12 from entering into the plies of the wire. Such coating is extremely effective not only for preventing corrosion of the wire but also for preventing contamination of the wire and for improving the smoothness with which the wire can be manipulated.

Obviously, numerous modifications and variations of the present invention are possible in the light of the above teachings. It is therefore to be understood that within the scope of the claims appended hereto the invention may be practiced otherwise than as specifically disclosed herein.

What is claimed is:

1. In an endoscope including a manipulator unit and a forward elongated insertion portion extending from the manipulator unit, forceps-control means movably mounted in a forward region of the insertion portion for selectively controlling the position of forceps at the forward region of the insertion portion, an operating wire guide tube extending within the insertion portion towards the manipulator unit, and an operating wire extending through and being guided by the wire guide tube having two ends, a first end of said operating wire being connected to the forceps-control means so that the position of the forceps can be controlled from the manipulator unit through displacement of the operating wire which thereby moves the forceps-control means, an apparatus for cleaning and/or sterilizing the operating wire guide tube, comprising:

a control shaft guide tube connected to said wire guide tube in fluid communication therewith;

a tubular control shaft mounted for guided forward and rearward longitudinal movement within said control shaft guide tube in a piston-like manner, said control shaft being connected to the second end of said operating wire which extends through and is guided by the wire guide tube within the forward elongated insertion portion of the endoscope;

sealing means for providing a substantially fluid-tight seal between said tubular control shaft and said control shaft guide tube;

fluid passage means provided in said tubular control shaft communicating with said control shaft guide tube, said fluid passage means comprising a fluid passage formed in said tubular control shaft, one end of said passage opening rearwardly of said sealing means and the other end of said passage opening forwardly of said sealing means and communicating with said control shaft guide tube;

a flexible tube having two ends, a first end being connected to said tubular control shaft for movement therewith and sealed in fluid communication to said one end of said fluid passage, said flexible tube including a slackened length portion of the form of a looped section of said flexible tube, said looped section of said flexible tube having a particular radial dimension for a respective position of said tubular control shaft, said looped tube section being situated such that movement of said tubular control shaft to which said first end of said flexible tube is connected in a rearward direction causes the dimension of said looped tube section to expand; and fluid inlet means externally provided on said manipulator unit with the second end of said flexible tube communicating therewith for injecting cleaning fluid or the like into said flexible tube;

whereby due to the presence of the looped section of the flexible tube, the relative increase in the volume of a tube system including the wire guide tube, the control shaft guide tube situtated forwardly of said sealing means, the fluid passage of said control shaft and the flexible tube as the control shaft is moved in a rearward direction within the control shaft guide tube and the consequent relative decrease in pressure in the tube system caused thereby is significantly less than when the flexible tube does not include the looped section.

2. The combination of claim 1 wherein said control shaft guide tube is mounted in said manipulator unit.

3. The combination of claim 1 wherein said sealing means comprises an O-ring provided on said tubular control shaft which engages the inner surface of said control shaft guide tube.

4. The combination of claim 1 wherein said fluid passage comprises a substantially axial bore formed in said tubular control shaft having a rearward portion opening from the rear end of said control shaft to constitute said one end of said passage, and at least one substantially radial opening fluidly interconnecting said control shaft guide tube and a forward portion of said axial bore, said radial opening constituting said other end of said passage.

5. The combination of claim 1 wherein said fluid inlet means comprises a mouthpiece provided externally on said manipulator unit.

6. The combination of claim 5 wherein said mouthpiece is located on a rear side of said manipulator unit away from said tubular control shaft.

7. The combination of claim 1 wherein said flexible tube includes a forward section extending between said control shaft to which said first end of said flexible tube is connected and said looped tube section, said forward tube section being substantially coaxial with said guide tube and control shaft and substantially tangential to said looped tube section.

8. The combination of claim 1 wherein said manipulator unit includes at least one operating button and said looped tube section is wound around said operating button.

9. The combination of claim 1 wherein said wire guide tube has an inner diameter which is greater than about 0.8 mm.

* * * * *